(12) United States Patent
Hawkins et al.

(10) Patent No.: US 9,220,521 B2
(45) Date of Patent: Dec. 29, 2015

(54) SHOCKWAVE CATHETER

(71) Applicant: SHOCKWAVE MEDICAL, INC., Fremont, CA (US)

(72) Inventors: Daniel Hawkins, Pleasanton, CA (US); John M. Adams, Snohomish, WA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 331 days.

(21) Appl. No.: 13/957,276

(22) Filed: Aug. 1, 2013

(65) Prior Publication Data

US 2014/0163592 A1 Jun. 12, 2014

Related U.S. Application Data

(60) Provisional application No. 61/679,911, filed on Aug. 6, 2012.

(51) Int. Cl.
*A61B 17/22* (2006.01)

(52) U.S. Cl.
CPC ..... *A61B 17/22004* (2013.01); *A61B 17/22012* (2013.01); *A61B 2017/22025* (2013.01); *A61B 2017/22051* (2013.01); *A61B 2017/22098* (2013.01)

(58) Field of Classification Search
CPC ............. A61B 17/225; A61B 17/2251; A61B 17/320068; A61B 17/22004; A61B 17/22012; A61B 17/22029; A61B 17/22022; A61B 17/22021; A61B 2017/22007; A61B 2017/22008; A61B 2017/22011; A61B 2017/22025; A61B 2017/22027; A61B 2017/22051; A61B 2017/22098; A61N 1/056; A61N 1/38; A61M 2025/0166; A61M 2025/1047

See application file for complete search history.

(56) References Cited

U.S. PATENT DOCUMENTS

| | | |
|---|---|---|
| 3,785,382 A | 1/1974 | Schmidt et al. |
| 3,902,499 A | 9/1975 | Shene |
| 4,027,674 A | 6/1977 | Tessler et al. |
| 4,030,505 A | 6/1977 | Tessler |
| 4,662,126 A | 5/1987 | Malcolm |
| 4,685,458 A | 8/1987 | Leckrone |
| 4,809,682 A | 3/1989 | Forssmann et al. |
| 5,009,232 A | 4/1991 | Hassler et al. |
| 5,046,503 A | 9/1991 | Schneiderman |

(Continued)

FOREIGN PATENT DOCUMENTS

| | | |
|---|---|---|
| CN | 101043914 A | 9/2007 |
| DE | 3038445 A1 | 5/1982 |

(Continued)

OTHER PUBLICATIONS

Final Office Action received for U.S. Appl. No. 12/482,995, mailed on Jul. 22, 2011, 14 pages.

(Continued)

*Primary Examiner* — Sarah W Aleman
(74) *Attorney, Agent, or Firm* — Morrison & Foerster LLP (57) ABSTRACT

A catheter, for use, for example, in valvuloplasty, includes an elongated body and an inflatable balloon carried by the elongated body. The balloon has an inner surface and an outer surface. The catheter further includes at least one shock wave source within the inflatable balloon and a follower arrangement that maintains the at least one shock wave source a substantially fixed distance from the inner surface of the balloon.

20 Claims, 4 Drawing Sheets

(56) References Cited

U.S. PATENT DOCUMENTS

| | | |
|---|---|---|
| 5,078,717 A | 1/1992 | Parins et al. |
| 5,103,804 A | 4/1992 | Abele et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,246,447 A | 9/1993 | Rosen et al. |
| 5,281,231 A | 1/1994 | Rosen et al. |
| 5,295,958 A | 3/1994 | Shturman |
| 5,324,255 A | 6/1994 | Passafaro et al. |
| 5,336,234 A | 8/1994 | Vigil et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | de la Torre et al. |
| 5,846,218 A | 12/1998 | Brisken et al. |
| 6,007,530 A | 12/1999 | Doernhoefer et al. |
| 6,033,371 A | 3/2000 | Torre et al. |
| 6,083,232 A | 7/2000 | Cox |
| 6,113,560 A | 9/2000 | Simnacher |
| 6,210,408 B1 | 4/2001 | Chandrasekaran et al. |
| 6,217,531 B1 | 4/2001 | Reitmajer |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,061 B1 | 8/2002 | Wenner et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,569,032 B2 | 8/2009 | Naimark et al. |
| 8,162,859 B2 | 4/2012 | Schultheiss et al. |
| 8,556,813 B2 | 10/2013 | Cioanta et al. |
| 8,574,247 B2 | 11/2013 | Adams et al. |
| 8,728,091 B2 | 5/2014 | Hakala et al. |
| 2001/0044596 A1 | 11/2001 | Jaafar |
| 2002/0177889 A1 | 11/2002 | Brisken et al. |
| 2003/0163081 A1 | 8/2003 | Constantz et al. |
| 2003/0229370 A1 | 12/2003 | Miller |
| 2004/0044308 A1 | 3/2004 | Naimark et al. |
| 2004/0082859 A1 | 4/2004 | Schaer |
| 2004/0097996 A1 | 5/2004 | Rabiner et al. |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0090846 A1 | 4/2005 | Pedersen et al. |
| 2005/0171527 A1 | 8/2005 | Bhola |
| 2005/0245866 A1 | 11/2005 | Azizi |
| 2005/0251131 A1 | 11/2005 | Lesh |
| 2006/0004286 A1 | 1/2006 | Chang et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2007/0088380 A1 | 4/2007 | Hirszowicz et al. |
| 2007/0129667 A1 | 6/2007 | Tiedtke et al. |
| 2007/0239082 A1 | 10/2007 | Schultheiss et al. |
| 2007/0244423 A1 | 10/2007 | Zumeris et al. |
| 2007/0299481 A1 | 12/2007 | Syed et al. |
| 2008/0077165 A1 | 3/2008 | Murphy |
| 2008/0097251 A1 | 4/2008 | Babaev |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0121322 A1 | 5/2010 | Swanson |
| 2010/0305565 A1 | 12/2010 | Truckai et al. |
| 2010/0324554 A1 | 12/2010 | Gifford et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0295227 A1 | 12/2011 | Hawkins et al. |
| 2012/0116289 A1 | 5/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0116714 A1 | 5/2013 | Adams et al. |
| 2014/0005576 A1 | 1/2014 | Adams et al. |
| 2014/0039513 A1 | 2/2014 | Hakala et al. |
| 2014/0039514 A1 | 2/2014 | Adams et al. |
| 2014/0046353 A1 | 2/2014 | Adams |
| 2014/0052147 A1 | 2/2014 | Hakala et al. |
| 2014/0214061 A1 | 7/2014 | Adams et al. |
| 2014/0243820 A1 | 8/2014 | Adams et al. |

FOREIGN PATENT DOCUMENTS

| | | |
|---|---|---|
| EP | 0442199 A2 | 8/1991 |
| EP | 0571306 A1 | 11/1993 |
| JP | 62-275446 A | 11/1987 |
| JP | 3-63059 A | 3/1991 |
| JP | 6-125915 A | 5/1994 |
| JP | 7-47135 A | 2/1995 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004-81374 A | 3/2004 |
| JP | 2004-357792 A | 12/2004 |
| JP | 2005-95410 A | 4/2005 |
| JP | 2005-515825 A | 6/2005 |
| JP | 2006-516465 A | 7/2006 |
| JP | 2008-506447 A | 3/2008 |
| JP | 2011-528963 A | 12/2011 |
| WO | 96/24297 A1 | 8/1996 |
| WO | 2004/069072 A2 | 8/2004 |
| WO | 2006/006169 A2 | 1/2006 |
| WO | 2006/127158 A2 | 11/2006 |
| WO | 2007/088546 A2 | 8/2007 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/069025 A1 | 6/2011 |
| WO | 2011/143468 A2 | 11/2011 |
| WO | 2013/070750 A1 | 5/2013 |

OTHER PUBLICATIONS

Non Final Office Action received for U.S. Appl. No. 12/482,995, mailed on Aug. 13, 2014, 10 pages.

Final Office Action received for U.S. Appl. No. 13/049,199 mailed on Aug. 11, 2014, 8 pages.

Notice of Allowance received for U.S. Appl. No. 13/831,543, mailed on Oct. 8, 2014, 14 pages.

Notice of Allowance received for U.S. Appl. No. 14/061,554, mailed on Apr. 25, 2014, 8 pages.

Non-Final Office Action received for U.S. Appl. No. 14/271,342, mailed on Sep. 2, 2014, 6 pages.

Notice of Acceptance Received for Australian Patent Application No. 2009257368, mailed on Aug. 28, 2014, 2 pages.

(56) References Cited

OTHER PUBLICATIONS

Office Action Received for Japanese Patent Application No. 2011-513694, mailed on Jun. 10, 2014, 2 pages (See Communication under 37 CFR § 1.98(a) (3)).
Office Action Received for Japanese Patent Application No. 2011-534914, mailed on Jul. 15, 2014, 3 pages (1 page of English Translation and 2 pages).
International Written Opinion received for PCT Patent Application No. PCT/US2009/063354, mailed on Jun. 11, 2010, 4 pages.
International Preliminary Report on Patentability received for PCT Patent Application No. PCT/US2012/063925, mailed on May 22, 2014, 12 pages.
Doug Hakala, "Unpublished U.S. Appl. No. 14/515,130, filed Oct. 15, 2014, titled "Low Profile Electrodes for an Angioplasty Shock Wave Catheter"".
Non Final Office Action received for U.S. Appl. No. 13/207,381, mailed on Feb. 22, 2013, 7 pages.
Non Final Office Action received for U.S. Appl. No. 13/232,730, mailed on Apr. 23, 2013, 10 pages.
Adams et al., Unpublished U.S. Appl. No. 14/229,735, filed Mar. 28, 2014, titled "Shock Wave Valvuloplasty Device with Moveable Shock Wave Generator".
Adams et al., Unpublished U.S. Appl. No. 14/271,342, filed May 6, 2014, titled "Shock Wave Balloon Catheter with Multiple Shock Wave Sources", 21 pages.
Office Action received for Australian Patent Application No. 2009257368, issued on Apr. 28, 2014, 4 pages.
Notice of Allowance received for U.S. Appl. No. 14/046,635, mailed on Dec. 17, 2013, 7 pages.
Extended European Search Report and Search Opinion received for EP Patent Application No. 09825393.3, mailed on Feb. 28, 2013, 6 pages.
International Search Report received for PCT Patent Application No. PCT/US2009/047070, mailed on Jan. 19, 2010, 4 pages.
International Preliminary Report on Patentability received for PCT Patent Application No. PCT/US2009/063354, mailed on May 19, 2011, 6 pages.
International Search Report received for PCT Patent Application No. PCT/US2009/063354, mailed on Jun. 11, 2010, 3 pages.
International Preliminary Report on Patentability received for PCT Patent Application No. PCT/US2011/047070, mailed on Feb. 21, 2013, 7 pages.
International Written Opinion received for PCT Patent Application No. PCT/US2011/047070, mailed on May 1, 2012, 5 pages.
International Preliminary Report on Patentability received for PCT Patent Application No. PCT/US2011/051606, issued on May 14, 2013, 6 pages.
International Search Report and Written Opinion received for PCT Patent Application No. PCT/US2011/051606, mailed on Apr. 24, 2012, 9 pages.
International Search Report received for PCT Patent Application No. PCT/US2012/063925, mailed on Mar. 25, 2013, 3 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/054104, mailed on Oct. 22, 2013, 12 pages.
International Search Report and Written Opinion received for PCT Patent Application No. PCT/US2013/053292, mailed on Nov. 4, 2013, 14 pages.
Extended European Search Report (includes Supplementary European Search Report and Search Opinion) received for European Patent Application No. 097636401, mailed on Oct. 10, 2013, 5 pages.
Notice of Allowance received for U.S. Appl. No. 13/291,875, mailed on Sep. 17, 2013, 11 pages.
Non Final Office Action received for U.S. Appl. No. 12/482,995, mailed on Jul. 12, 2013, 11 pages.
Non Final Office Action received for U.S. Appl. No. 13/291,875 mailed on Feb. 28, 2013, 8 pages.
Hawkins et al., U.S. Appl. No. 61/061,170, filed Jun. 13, 2008, titled "Shockwave Balloon Catheter System".
Office Action received for Australian Patent Application No. 2009257368, issued on Jul. 31, 2013, 4 pages.
Office Action received for Chinese Patent Application No. 200980153687.X, mailed on Dec. 26, 2012, 11 pages.
Office Action received for Chinese Patent Application No. 200980153687.X, mailed on Jul. 11, 2013, 11 pages.
Office Action received for Japanese Patent Application No. 2011-513694, mailed on Aug. 27, 2013, 6 pages (3 pages of English Translation and 3 pages).
Office Action received for Japanese Patent Application No. 2011-534914, mailed on Oct. 1, 2013, 5 pages (2 pages of English Translation and 3 pages).
Final Office Action received for U.S. Appl. No. 12/611,997, mailed on Oct. 24, 2013, 10 pages.
Final Office Action received for U.S. Appl. No. 13/207,381, mailed on Nov. 7, 2013, 7 pages.
Office Action received for Australian Patent Application No. 2009313507, issued on Nov. 13, 2013, 3 pages.
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Final Office Action received for U.S. Appl. No. 12/482,995, mailed on Feb. 20, 2014, 11 pages.
Non Final Office Action received for U.S. Appl. No. 12/501,619, mailed on Jan. 28, 2014, 10 pages.
Non Final Office Action received for U.S. Appl. No. 12/611,997, mailed on Feb. 13, 2014, 9 pages.
Non Final Office Action received for U.S. Appl. No. 13/049,199, mailed on Feb. 4, 2014, 8 pages.
Non Final Office Action received for U.S. Appl. No. 13/207,381, mailed on Feb. 25, 2014, 8 pages.
Non Final Office Action received for U.S. Appl. No. 14/061,554, mailed on Mar. 12, 2014, 14 pages.
Non Final Office Action received for U.S. Appl. No. 12/482,995, mailed on Feb. 11, 2011, 27 pages.
Non Final Office Action received for U.S. Appl. No. 12/501,619, mailed on Nov. 3, 2011, 10 pages.
Final Office Action received for U.S. Appl. No. 12/501,619, mailed on Feb. 21, 2012, 12 pages.
Non Final Office Action received for U.S. Appl. No. 12/611,997, mailed on Jun. 21, 2011, 13 pages.
Final Office Action received for U.S. Appl. No. 12/611,997, mailed on Nov. 10, 2011, 15 pages.
Non Final Office Action received for U.S. Appl. No. 12/611,997, mailed on Aug. 24, 2012, 11 pages.
Final Office Action received for U.S. Appl. No. 12/611,997, mailed on Dec. 11, 2012, 9 pages.
Non Final Office Action received for U.S. Appl. No. 12/611,997, mailed on Apr. 8, 2013, 9 pages.
Non Final Office Action received for U.S. Appl. No. 13/049,199, mailed on Dec. 12, 2011, 10 pages.
Final Office Action received for U.S. Appl. No. 13/049,199, mailed on Apr. 4, 2012, 10 pages.
Non Final Office Action received for U.S. Appl. No. 13/207,381, mailed on Jun. 12, 2012, 6 pages.
Final Office Action received for U.S. Appl. No. 13/207,381, mailed on Nov. 2, 2012, 7 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.

(56) References Cited

OTHER PUBLICATIONS

Non-Final Office Action received for U.S. Appl. No. 13/646,583, mailed on Oct. 31, 2014, 8 pages.

Written Opinon received for PCT Patent Application No. PCT/US2009/047070, mailed on Jan. 19, 2010, 5 pages.

International Preliminary Report on Patentability received for PCT Patent Application No. PCT/US2009/047070, mailed on Dec. 23, 2010, 7 pages.

FIG. 6

SHOCKWAVE CATHETER

CLAIM OF PRIORITY

The present application claims the benefit of U.S. provisional patent application Ser. No. 61/679,911, filed Aug. 6, 2012, which application is incorporated herein by reference in its entirety.

BACKGROUND

Patients suffering from aortic valve stenosis often have calcified aortic valve leaflets. Shockwave therapy for the treatment of aortic valve stenosis has been previously described in, for example U.S. Pat. Pub. No. 2010/0114020A1, the disclosure of which is incorporated herein by reference. As described therein, a valvuloplasty catheter includes a balloon that is inflatable with a fluid. When the balloon is inflated, it is configured to be adjacent valve leaflets, such as the valve leaflets of an aortic valve. Within the balloon, there is disposed a shock wave generator. The shock wave generator includes at least two electrodes. When a high voltage pulse is applied across the electrodes, an electrical arc is formed. The electrical arc creates a shock wave within the fluid that propagates to the balloon walls to impinge upon the valve leaflets and the calcification on the valve. Repeated shock waves cause the calcification to break-up.

The distance between the shock wave generator (the electrodes) and the valve leaflets of the catheter described above is variable and not controlled. It has been found that shock wave therapy designed to break calcium deposits is most effective at certain distances from a radiating shock wave source. This is particularly the case when the source is a point source without a reflector. Generally, the effectiveness of the shock waves falls off or decreases with the square of the distance from the source.

When a valvuloplasty balloon and a shock wave generator are combined as described above, the distance between the shock wave generator and the balloon walls generally increases as the valve is opened by balloon expansion occasioned by effective treatment and valvuloplasty pressure. As the distance changes and becomes greater, the effectiveness of the therapy decreases. This increases both the time and the number of shock waves required for complete and effective treatment. Hence, there is a need for a shock wave valvuloplasty catheter that maintains therapy effectiveness at a desired level until the valve being treated is dilated the desired amount.

SUMMARY

According to embodiments shown and described herein, a catheter, which may find use, for example, in valvuloplasty, includes an elongated body and an inflatable balloon carried by the elongated body. The balloon has an inner surface and an outer surface. The catheter further includes at least one shock wave source within the inflatable balloon and a follower arrangement that maintains the at least one shock wave source a substantially fixed distance from the inner surface of the balloon.

The follower arrangement may be carried by the at least one shock wave source within the inflatable balloon. The at least one shock wave source may be an arc generator including an electrode pair.

The follower arrangement may include at least one stand-off extending from the electrode pair. The stand-off may be formed of flexible material.

The arc generator may include an elongated lead. The electrode pair may be carried by the elongated lead, and the elongated lead may be biased in a direction towards the inner surface of the inflatable balloon. The elongated lead may include at least one bend that biases the elongated lead towards the inner surface of the inflatable balloon.

The catheter may further include a biasing member carried by the elongated lead that biases the elongated lead towards the inner surface of the inflatable balloon. The biasing member may be a spring.

The at least one shock wave source may include an arc generator. The follower arrangement may include a stand-off carried by the arc generator and the arc generator may be biased towards the inner surface of the inflatable balloon.

The catheter may further include a frame structure that carries the at least one shock wave source. The frame structure may be arranged to expand with inflation of the inflatable balloon to maintain the at least one shock wave source a substantially fixed distance from the inner surface of the balloon. The frame structure may include at least one stand-off adjacent the at least one shock wave source to maintain the at least one shock wave source a substantially fixed distance from the inner surface of the balloon.

In other embodiments, a method includes the steps of providing a catheter including an elongated body, an inflatable balloon carried by the elongated body and having an inner surface and an outer surface, and at least one shock wave source within the inflatable balloon. The method further includes the steps of inserting the catheter into a vein or artery of a patient and placing the balloon adjacent to an anatomical structure to be treated, inflating the balloon with a fluid, causing the shock wave source to provide shock waves within the balloon that propagate through the liquid to treat the anatomical structure, and maintaining the at least one shock wave source a substantially fixed distance from the inner surface of the balloon while the shock waves are provided by the at least one shock wave source.

The catheter may further include a follower carried by the shock wave generator, and the maintaining step may include biasing the follower against the inner wall of the balloon.

The catheter may include a frame structure that carries the at least one shock wave source. The maintaining step may include expanding the frame structure with inflation of the inflatable balloon to maintain the at least one shock wave source the substantially fixed distance from the inner surface of the balloon.

BRIEF DESCRIPTION OF THE DRAWINGS

The features of the present invention which are believed to be novel are set forth with particularity in the appended claims. The various described embodiments of the invention, together with representative features and advantages thereof, may best be understood by making reference to the following description taken in conjunction with the accompanying drawings, in the several figures of which like reference numerals identify identical elements, and wherein:

DETAILED DESCRIPTION

Figure 1:
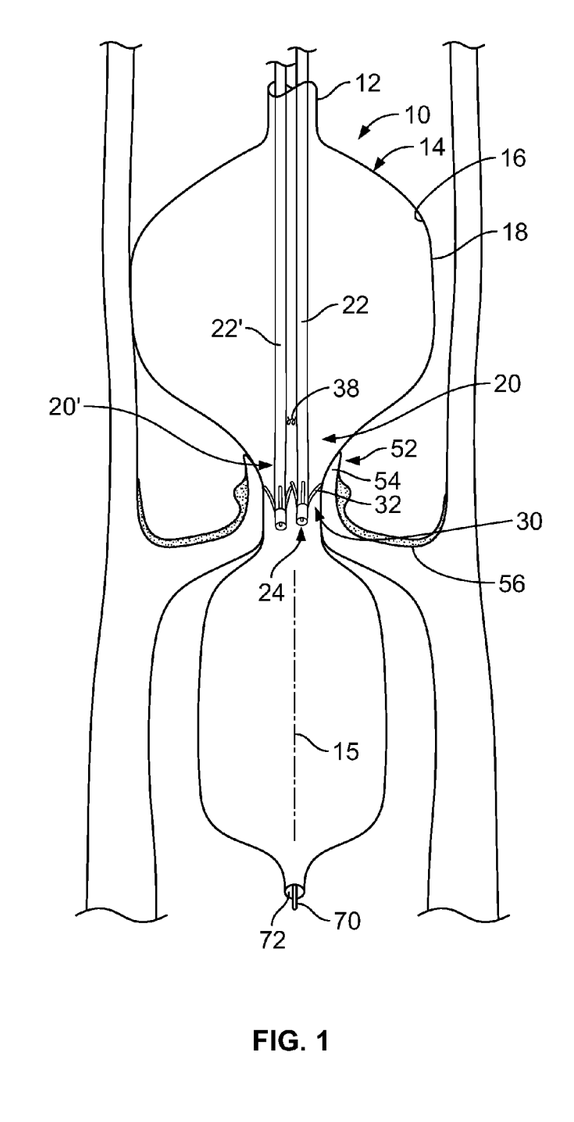
FIG. 1 is a partial cut away view of a heart and a catheter embodying aspects of the invention within the aortic valve of the heart.

Referring now to FIG. 1, it is a partial cut away view of the aorta 50 of a heart and a catheter 10 embodying aspects of the invention within the aortic valve 52 of the heart. The catheter 10 generally includes an elongated body 12, an inflatable balloon 14 carried by the elongated body 12, at least one shock wave source 20 within the inflatable balloon 14, and a follower arrangement 30. The balloon includes an inner surface 16 and an outer surface 18. The follower arrangement 30 is carried by the shock wave source 20. As will be seen subsequently, the follower arrangement maintains the at least one shock wave source 20 a substantially fixed distance from the inner surface 16 of the balloon.

The balloon 14 is inflatable through the elongated body 12 with a fluid such as, for example, saline. The balloon is configured so that when positioned within the aortic valve 52, its outer surface 18 substantially conforms to and is immediately adjacent to or in contact with the aortic valve leaflets 54 and the calcification 56 thereon.

The shock wave source 20 preferably is an arc generator that produces electrical arcs that form rapidly expanding and contracting steam bubbles within the balloon 14. The rapidly expanding and contracting steam bubbles form shock waves within the balloon 14 that propagate through the fluid within the balloon and impinge upon the inner surface 16 of the balloon 14 and the calcification 56. After repeated shock waves, the calcification is broken up to permit the aortic valve 52 to function. The follower arrangement 30 maintains the shock wave source a substantially fixed distance from the inner surface 16 of the balloon 14 and hence the valve leaflets 54 to maintain full effectiveness of the shock waves during the shock wave application procedure.

FIG. 1 also shows that the catheter 10 is arranged to accept a guide wire 70. The guide passes through a guide wire lumen 72 and serves to guide the catheter into an artery or vein to place the balloon adjacent an anatomical structure to be treated such as an aortic valve. Once the balloon is thus positioned, it may be inflated and the shock wave therapy begun.

Figure 2:
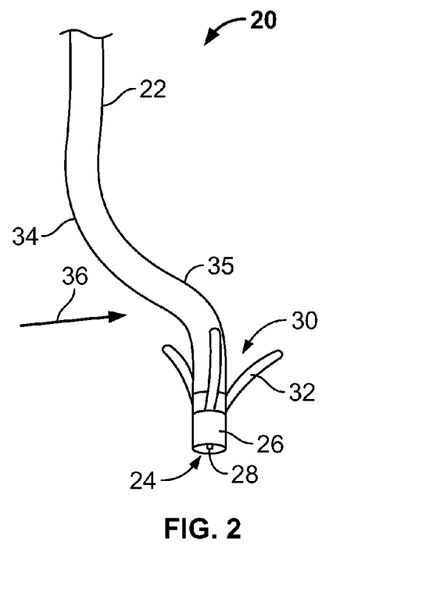
FIG. 2 is a side view of a shock wave generator which may be used to advantage within the catheter of FIG. 1 and which embodies aspects of the invention.

As may be seen in FIG. 2, the shock wave source or generator 20 includes an elongated lead 22 and an electrode pair 24 carried by the lead 22. The electrode pair 24 is formed by a pair of coaxially disposed electrodes including a ring electrode 26 and a center electrode 28. Voltage pulses are applied across electrodes 26 and 28 through the lead 22 to cause the arcs which produce the shock waves.

The catheter 10 of FIG. 1 includes two shock wave sources 20 and 20'. The shock wave source 20' may be identical to the shock wave source 20. Each shock wave source carries a follower arrangement. In the embodiment of FIG. 1, a spring 38 is attached to and in between the leads 22 and 22' of the shock wave sources 20 and 20', respectively. The spring 38 serves as a biasing member to force the electrode pairs of the shock wave sources and the follower arrangements off of the center axis 15 of the balloon 14 towards the inner surface 16 of the balloon 14.

Alternatively, or in addition, as may be seen in FIG. 2, the lead 22 may have permanent bends 34 and 35 formed therein. The bends bias the electrode pair 24 in the direction indicated by arrow 36 towards the inner surface 16 of the balloon 14.

Hence, FIG. 1 shows a valvuloplasty system having a catheter 10 according to some aspects of the invention that includes a valvuloplasty balloon 14 with two electrodes (electrode pair 24) disposed therein. The system is shown within an aortic valve 52 for treating calcification 56 on the valve leaflets 54. The electrodes are urged away from the center axis 15 of the balloon 14 toward the perimeter of the balloon 14 by a spring member 38. As may be appreciated, the spring member may be replaced by spring loading or biasing the leads 22 and 22' that carry the electrodes outwardly. The balloon 14 is shown within a severely stenosed valve 52. Stand offs 32 carried on electrodes maintain a substantially constant distance between electrodes and the walls of the balloon 14 and hence between the electrodes and the valve leaflets 54.

Further, FIG. 2 shows a detailed view of one electrode pair 24 and its lead 22. The standoffs 32 are formed by soft flexible arms that are designed to hold the electrode pair 24 off the balloon wall in non-touching relation to the balloon material. They are also designed to hold the tip of the electrode pair 24 a substantially constant distance, for example, 1-2 mm, from the balloon wall. At the same time, according to this embodiment, the elongated lead 22 has bends 34 and 35 to provide a predetermined bias toward the outside (away from the center axis) of the balloon.

Figure 3:
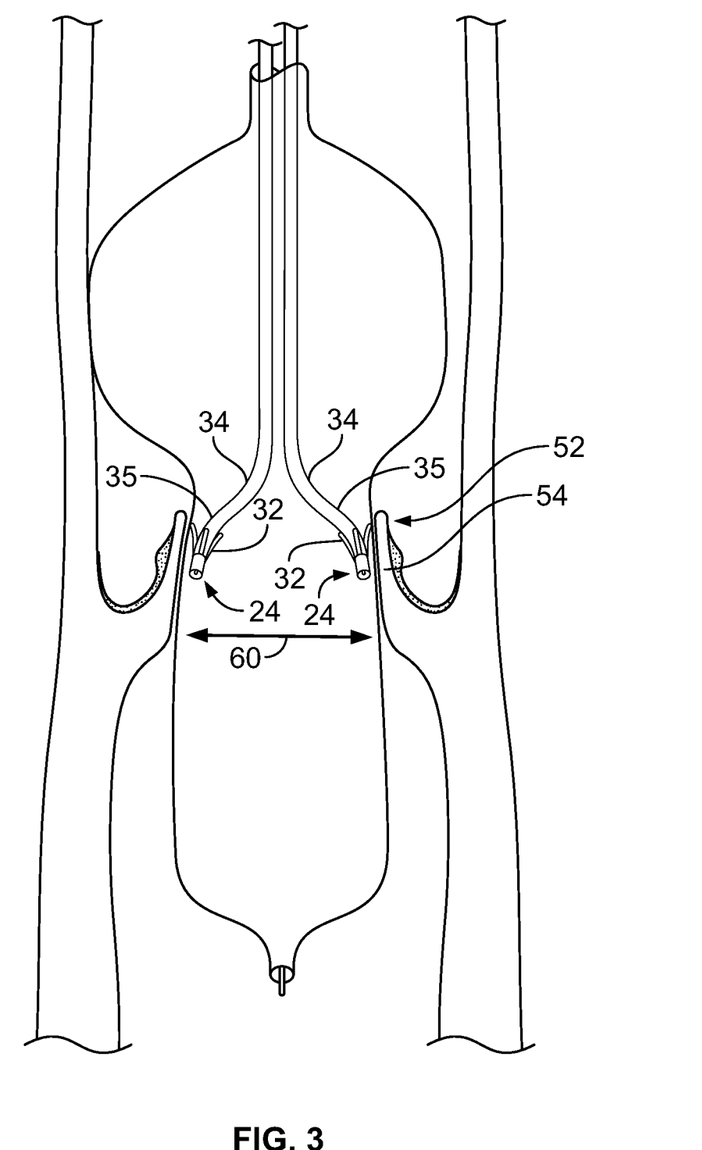
FIG. 3 is a partial cut away view of the heart of FIG. 1 illustrating the catheter as it is delivering therapy to the aortic valve of the heart.

FIG. 3 is a partial sectional view showing the valvuloplasty balloon 14 placed in an aortic valve 52 and after providing some treatment to break up or sever the calcium deposits 56 on the valve leaflets 52. The electrode pairs 24 have been held a substantially constant distance, for example about 1-2 mm, from the tissue by the stand offs since the electro-hydraulic shock therapy began. As the shock waves break the calcium, the opening 60 in the valve 52 slowly widens. Even though the valve is being opened wider, the distance between the electrode pairs 24 and the tissue of the leaflets 54 remains substantially constant, controlled by the stand offs 32 and the bends 34 and 35 in the electrode leads.

Figure 4:
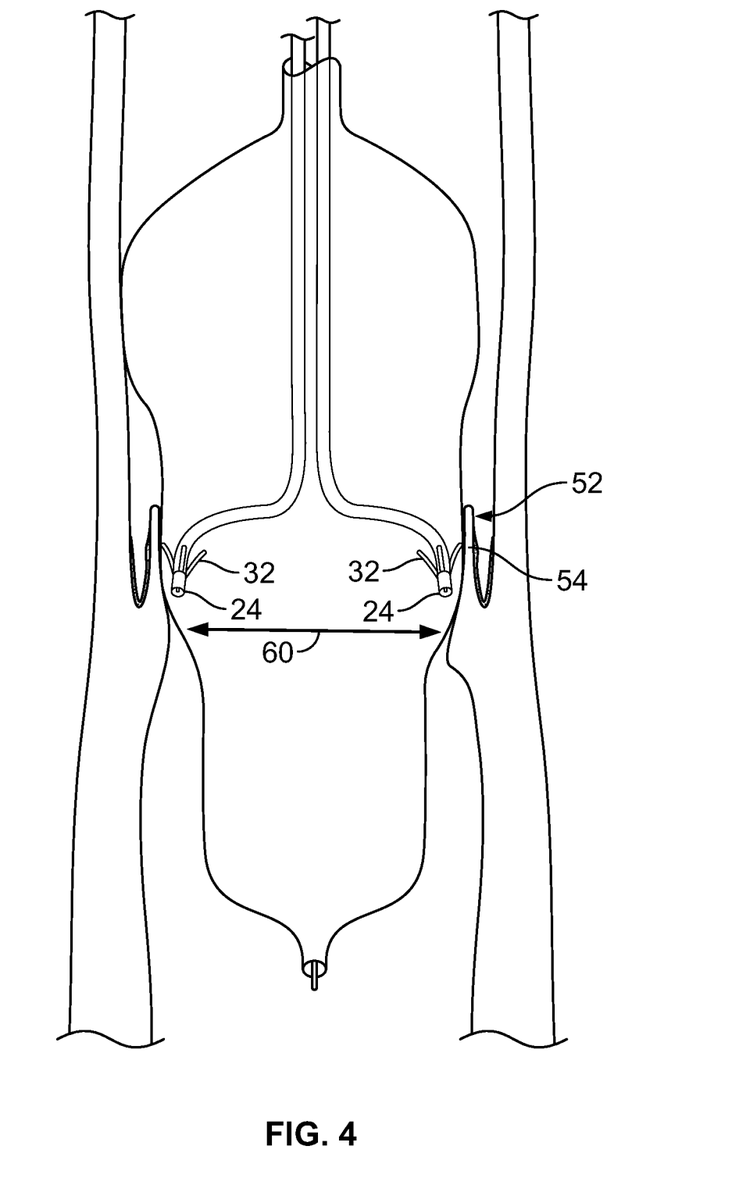
FIG. 4 is a partial cut away view of the heart of FIG. 1 illustrating the catheter upon completion of therapy to the aortic valve of the heart.

FIG. 4 shows a fully opened opening 60 of valve 52 expanded by the combination valvuloplasty balloon 14 and the shock wave therapy. The bias in the catheter and the standoffs hold the electrode pairs a substantially constant distance from the tissue of the valve being treated. For simplicity, only two electrode pairs are shown. However, in actual practice, as many as 3-9 electrode pair may typically be used. The electrode pairs 24 can be fired (provided with arc forming voltage) alternately or simultaneously. The calcium on the valve 52 and its softened valve leaflets 54 (and valve cusps) is now cracked making the valve much better prepared for the placement of a TAVI (Transcatheter Aortic-Valve Implantation) valve. In addition, the native valve 52 may function on its own without a replacement.

Figure 5:
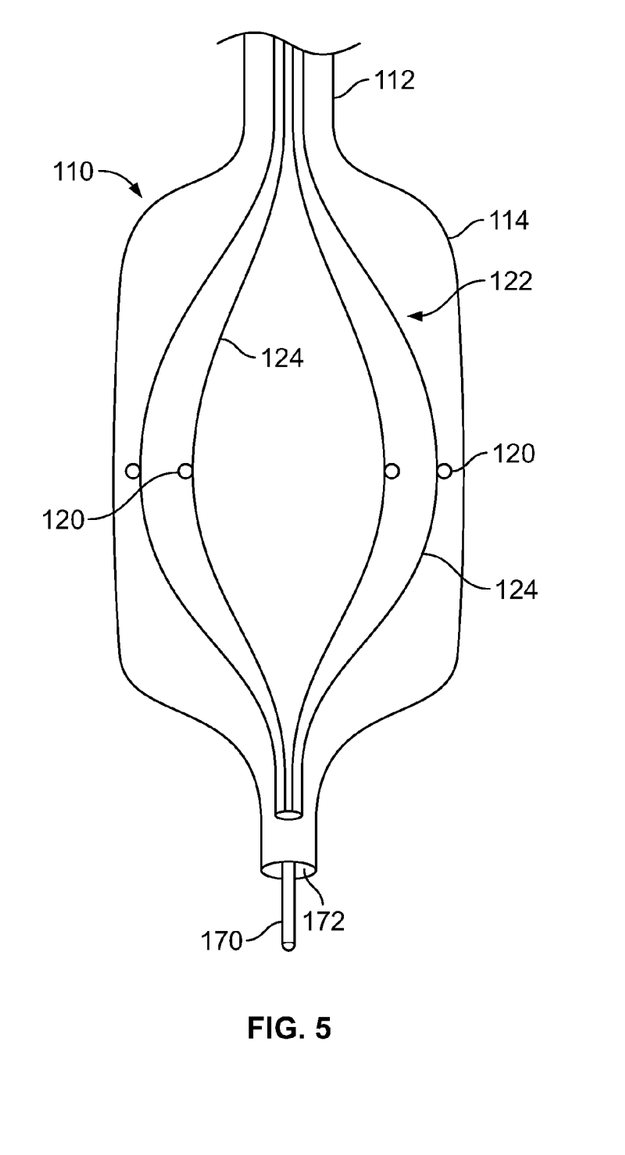
FIG. 5 is a partial cut away view of another heart and another catheter embodying further aspects of the invention within the aortic valve of the heart.

FIG. 5 shows an alternate embodiment. Here, a catheter 110 includes an elongated body 112 and an inflatable balloon 114, as in previous embodiments. Here, however, the shock wave sources 120, which may be electrode pairs, are mounted on a basket or frame structure 122 having basket arms or frame elements 124. The basket arms 124 may be formed of Nitinol and may be set to expand with the balloon 114 as the stenosis of the aortic valve being treated is softened and expanded by the shock waves.

Figure 6:
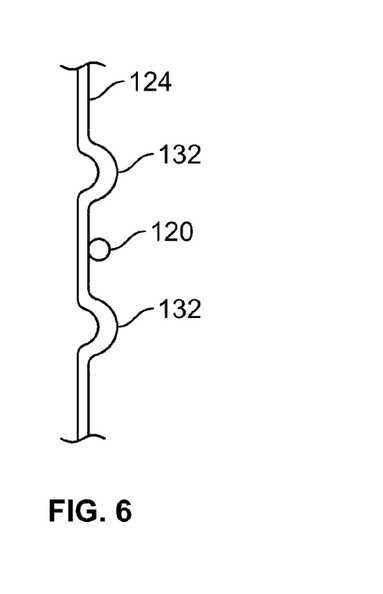
FIG. 6 is a partial view to an exploded scale illustrating particular aspects of the catheter of FIG. 5.

FIG. 6 shows the Nitinol arms 124 in greater detail with respect to the shock wave sources 120. Here it may be seen that the arms 124 may be configured with bumps or stand offs 132 to hold the shock wave sources 120 away from the balloon and tissue a substantially fix distance during the shock wave treatment.

FIG. 6 also shows that, as in previous embodiments, the catheter 112 may accommodate a guide wire 170. The guide wire 170 may be received within a guide wire lumen 172 and used, as previously described, to guide the catheter into proper position.

While particular embodiments of the present invention have been shown and described, modifications may be made, and it is therefore intended to cover in the appended claims all such changes and modifications which fall within the true spirit and scope of the invention.

What is claimed is:

1. A catheter comprising:
   an elongated body;
   an inflatable balloon carried by the elongated body, the balloon having an inner surface and an outer surface;
   at least one shock wave source within the inflatable balloon wherein the shock wave source is biased towards the inner surface of the balloon when the balloon is inflated; and
   a follower arrangement, said follower arrangement including a stand-off that maintains the at least one shock wave source a substantially fixed distance from the inner surface of the balloon when the balloon is inflated.

2. The catheter of claim 1, wherein the follower arrangement is carried by the at least one shock wave source within the inflatable balloon.

3. The catheter of claim 1, wherein the at least one shock wave source is an arc generator.

4. The catheter of claim 3, wherein the arc generator comprises an electrode pair.

5. The catheter of claim 4, wherein the stand-off extends from the electrode pair.

6. The catheter of claim 5, wherein the stand-off is formed of flexible material.

7. The catheter of claim 5, wherein the arc generator includes an elongated lead, wherein the electrode pair is carried by the elongated lead, and wherein the elongated lead is biased in a direction towards the inner surface of the inflatable balloon.

8. The catheter of claim 7, wherein the elongated lead includes at least one bend that biases the elongated lead towards the inner surface of the inflatable balloon.

9. The catheter of claim 7, further including a biasing member carried by the elongated lead that biases the elongated lead towards the inner surface of the inflatable balloon.

10. The catheter of claim 9, wherein the biasing member comprises a spring.

11. The catheter of claim 1, wherein the at least one shock wave source comprises an arc generator, wherein the stand-off is carried by the arc generator, and wherein the arc generator is biased towards the inner surface of the inflatable balloon.

12. The catheter of claim 1, further including a frame structure that carries the at least one shock wave source, wherein the frame structure expands with inflation of the inflatable balloon to maintain the at least one shock wave source the substantially fixed distance from the inner surface of the balloon.

13. The catheter of claim 12, wherein the frame structure includes the stand-off adjacent the at least one shock wave source to maintain the at least one shock wave source a substantially fixed distance from the inner surface of the balloon.

14. A method comprising:
   providing a catheter including an elongated body, an inflatable balloon carried by the elongated body, the balloon having an inner surface and an outer surface, and at least one shock wave source within the inflatable balloon;
   inserting the catheter into a vein or artery of a patient and placing the balloon adjacent to an anatomical structure to be treated;
   inflating the balloon with a liquid;
   biasing the shock wave source towards the inner surface of the balloon;
   causing the shock wave source to provide shock waves within the balloon that propagate through the liquid to treat the anatomical structure;
   maintaining the at least one shock wave source a substantially fixed distance from the inner surface of the balloon while the shock waves are provided by the at least one shock wave source.

15. The method of claim 14, wherein the catheter further includes a follower carried by the shock wave source, and wherein the maintaining step includes biasing the follower against the inner wall of the balloon.

16. The method of claim 14, wherein the catheter further includes a frame structure that carries the at least on shock wave source, and wherein the maintaining step includes expanding the frame structure with inflation of the inflatable balloon to maintain the at least one shock wave source a substantially fixed distance from the inner surface of the balloon.

17. A catheter comprising:
   an elongated body;
   an inflatable balloon carried by the elongated body, the balloon having an inner surface and an outer surface;
   an elongated lead carrying at least one shock wave source located within the inflatable balloon, wherein the lead is biased towards the inner surface of the balloon when the balloon is inflated; and
   a stand-off attached to the lead and configured to space the shock wave source away from the inner surface of the balloon when the balloon is inflated.

18. The catheter of claim 17 wherein the stand-off is formed from a flexible material.

19. The catheter of claim 17, wherein the at least one shock wave source is an arc generator.

20. The catheter of claim 19, wherein the arc generator comprises an electrode pair.

* * * * *

UNITED STATES PATENT AND TRADEMARK OFFICE
CERTIFICATE OF CORRECTION

PATENT NO.        : 9,220,521 B2
APPLICATION NO.   : 13/957276
DATED             : December 29, 2015
INVENTOR(S)       : Daniel Hawkins et al.

Page 1 of 1

It is certified that error appears in the above-identified patent and that said Letters Patent is hereby corrected as shown below:

In the Claims:

At column 6, claim number 14, line number 23, please replace "structure;" with

--structure; and--.

Signed and Sealed this
Twenty-third Day of August, 2016

Michelle K. Lee
*Director of the United States Patent and Trademark Office*